United States Patent [19]

Vorley et al.

[11] Patent Number: 5,216,016

[45] Date of Patent: Jun. 1, 1993

[54] INSECTICIDAL COMPOSITION

[75] Inventors: William Vorley, Basel; Friedrich Karrer, Zofingen; Francois Bourgeois, Birsfelden, all of Switzerland

[73] Assignee: Ciba-Geigy Corporation, Ardsley, N.Y.

[21] Appl. No.: 848,475

[22] Filed: Mar. 6, 1992

[30] Foreign Application Priority Data

Mar. 14, 1991 [CH]  Switzerland ............................ 780/91

[51] Int. Cl.$^5$ ...................... A01N 31/14; A01N 47/10
[52] U.S. Cl. ................................. 514/479; 514/721; 514/486
[58] Field of Search ..................... 514/479, 486, 721

[56] References Cited

U.S. PATENT DOCUMENTS

| | | | |
|---|---|---|---|
| 4,215,139 | 7/1980 | Fischer et al. | 424/300 |
| 4,413,010 | 11/1983 | Zurflüh | 514/486 |
| 4,885,162 | 12/1989 | Kawai et al. | 514/721 |
| 4,919,935 | 4/1990 | Dorn | 424/405 |
| 5,077,311 | 12/1991 | Karrer et al. | 514/486 |
| 5,082,860 | 1/1992 | Karrer et al. | 514/486 |

FOREIGN PATENT DOCUMENTS

| | | |
|---|---|---|
| 0004334 | 10/1979 | European Pat. Off. . |
| 0302389 | 2/1989 | European Pat. Off. . |
| 0309893 | 4/1989 | European Pat. Off. . |
| 0376279 | 7/1990 | European Pat. Off. . |
| 0404720 | 12/1990 | European Pat. Off. . |
| 3832656 | 4/1989 | Fed. Rep. of Germany . |
| 9104965 | 4/1991 | PCT Int'l Appl. . |

OTHER PUBLICATIONS

Derwent Abstract-JP-60,036,403 Feb. 25, 1985.
Pesticide Manual, 9th edition, 1991, pp. 105, 196, 201, 208, 209, 355, 371, 491, 504, 586 and 597.
Proceedings of the first Isia-Pacific Conference of Entomology, 1989, pp. 42 and 55.
Chemical Abstract 111 (23):214236r.

*Primary Examiner*—Allen J. Robinson
*Attorney, Agent, or Firm*—Kevin Mansfield; Edward McC. Roberts

[57] ABSTRACT

A novel synergistic insecticidal composition that comprises, in addition to carriers and/or other adjuvants or diluents, a component
A consisting of an insecticidal compound of formula I

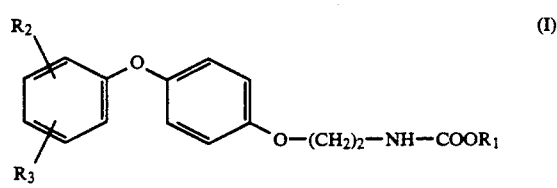

wherein $R_1$ is $C_1$-$C_3$alkyl, $R_2$ is halogen and $R_3$ is hydrogen or halogen, and also a component
B consisting of one or more insecticidal compounds selected from the group consisting of the compounds of formulae II to XV

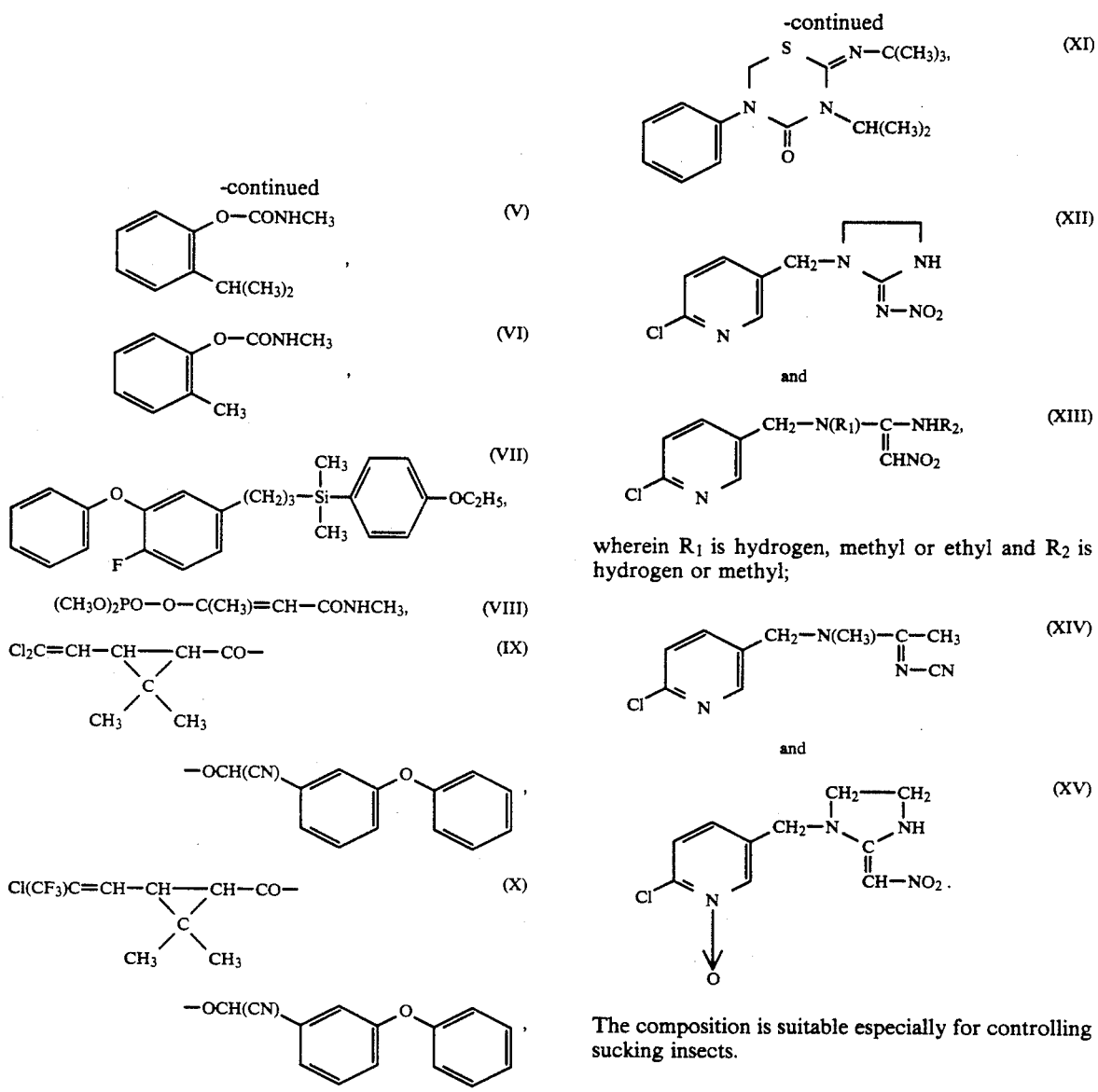
wherein R₁ is hydrogen, methyl or ethyl and R₂ is hydrogen or methyl;
The composition is suitable especially for controlling sucking insects.
21 Claims, No Drawings

INSECTICIDAL COMPOSITION

The present invention relates to a novel insecticidal pesticidal composition that comprises combinations of active ingredients as active component, to the use thereof for controlling noxious insects, and to the preparation of that composition.

Pest control is currently increasingly faced with difficulties. Important contributory factors in this connection are both the development by the pests to be controlled of resistance to the pesticides that are employed, and the environmental damage caused as a result of the increase in the active ingredient concentrations applied and the repeated application of active ingredients which is necessary for effective control of the pests. In order to avoid such detrimental ecological consequences, therefore, attempts are being made to reduce the rates of application of chemical substances. However, the use of low concentrations of active ingredient and insufficiently frequent application of active ingredients, which do not guarantee that the pest populations, including all development stages thereof, will be destroyed completely, encourage the emergence of resistant species of pest.

In order to avoid these disadvantages, therefore, it is desirable to make available for the control of pests, such as noxious insects, compositions that guarantee sufficiently high mortality even at low rates of application, and with as few applications as possible, and thus neither encourage the development of resistance nor pose a threat to the environment. Several attempts have therefore already been made to meet those requirements by combining different substances and making use of the potentiating effects which thereby occur. Mixtures of compounds from different classes, for example pyrethroids, carbamates and phosphoric acid esters, have already been described as synergistically active preparations in the field of pesticides (see EP Patent Application 309 893 and JP Patent Publication J6 0036.403).

The problem underlying the present invention is essentially to ensure a maximum and long-lasting insecticidal effect, in the sense of complete destruction of the noxious insects to be controlled and protection of the treated crops, throughout the entire season, using as small an amount of active ingredients as possible, the said effect being achieved with minimum damage to the environment and with optimum protection of beneficial organisms.

The present invention proposes a novel composition that has synergistic activity and is suitable for controlling insects and that comprises, in addition to carriers and/or other adjuvants or diluents, a component A consisting of an insecticidal compound of formula I

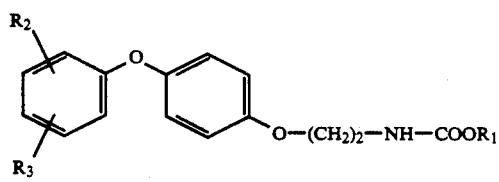

wherein $R_1$ is $C_1$-$C_3$alkyl, $R_2$ is halogen and $R_3$ is hydrogen or halogen, and also a component B consisting of one or more insecticidal compounds selected from the group consisting of the compounds of formulae II to XV

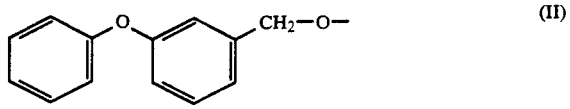

(II)

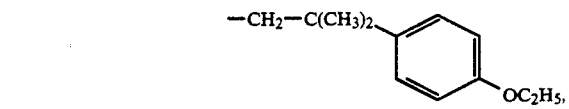

(III)

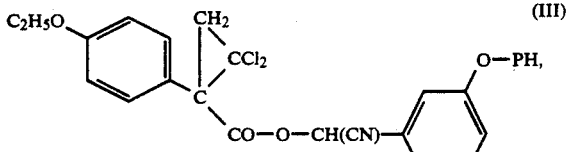

(IV)

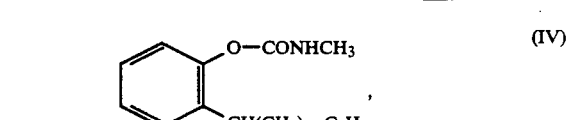

(V)

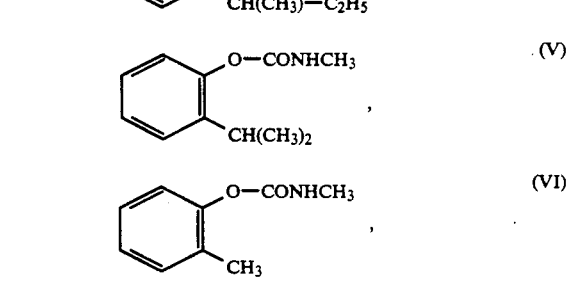

(VI)

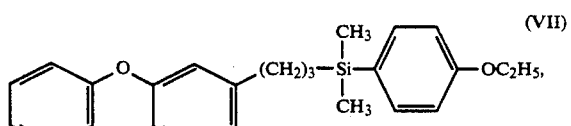

(VII)

$(CH_3O)_2PO-O-C(CH_3)=CH-CONHCH_3$, (VIII)

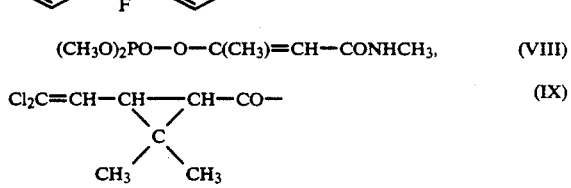

(IX)

,

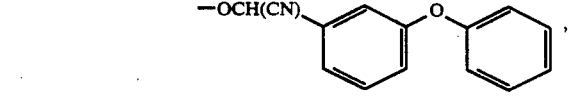

(X)

,

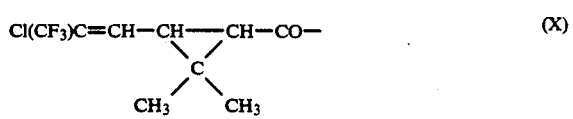

(XI)

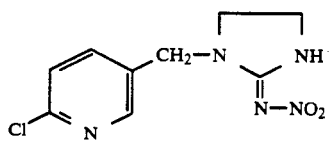

(XII)

and

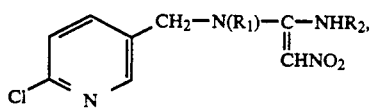

(XIII)

wherein $R_1$ is hydrogen, methyl or ethyl and $R_2$ is hydrogen or methyl;

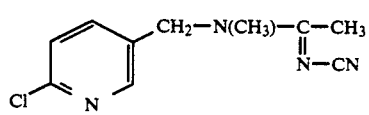

(XIV)

and

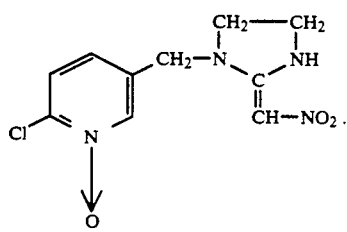

(XV)

The compounds of formulae VIII to X, XIII and XV are mixtures of cis- and trans-isomers, it being possible for the ratio of cis- to trans-forms to be high or low, or are in the form of pure cis- or trans-isomers. The compounds of formulae XI to XV are to be understood as including also their possible tautomeric forms.

According to the invention, preference is given to synergistic compositions that comprise as component A an insecticidal compound of formula I wherein $R_1$ is $C_1-C_3$alkyl, $R_2$ is fluorine or chlorine and $R_3$ is hydrogen or fluorine, or wherein $R_1$ is $C_1-C_3$alkyl, $R_2$ is 4-fluorine and $R_3$ is hydrogen, or wherein $R_2$ is 3-fluorine and $R_3$ is 5-fluorine or $R_2$ is 3-chlorine and $R_3$ is hydrogen.

Special preference is given on account of their biological activity to those synergistic compositions according to the invention that comprise as component A a compound of formula Ia, Ib or Ic:

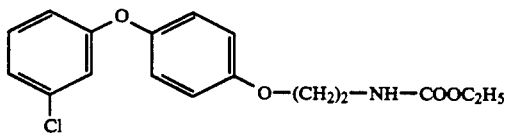

(Ia)

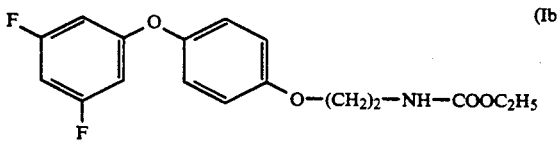

(Ib)

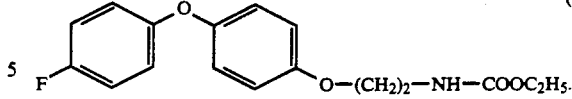

(Ic)

Special mention is also to be made of those compositions according to the invention that comprise as component B a compound of the above formulae II to XIII, preferably of formula II, IV, V, XII or XIII. Special preference is given on account of its biological properties to the combination of the compound of formula Ia as component A with the compound of formula II as component B.

Of the compounds of component B that fall within the scope of the general formula XIII, the compound of formula XIIIa

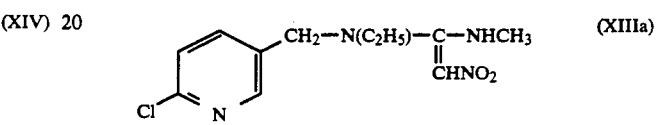

(XIIIa)

is of special importance as regards activity.

The compounds of formula I (component A) are in principle known and can be obtained according to known preparation methods (see, for example, EP Patent Applications Nos. 4.334 and 404.720 and also DE-OS No. 3.832.056).

The following compounds that fall within the scope of formula I are of special importance for the invention:

TABLE I

| Comp. No. | $R_1$ | $R_2$ | $R_3$ | Physical data |
|---|---|---|---|---|
| Ia | $-C_2H_5$ | 3-Cl | H | m.p. 45–46° C. |
| Ib | $-C_2H_5$ | 3-F | 5-F | m.p. 54–55° C. |
| Ic | $-C_2H_5$ | 4-F | H | m.p. 82–83° C. |
| Id | $-C_2H_5$ | 3-Cl | 5-Cl | $n_D^{20}$: 1.5693 |
| Ie | $-C_2H_5$ | 3-F | H | $n_D^{20}$: 1.5430 |
| If | $-C_2H_5$ | 3-F | 4-F | m.p. 60–61° C. |
| Ig | $-C_2H_5$ | 2-F | 4-F | $n_D^{20}$: 1.5340 |
| Ih | $-C_2H_5$ | 4-Cl | H | m.p. 98–99° C. |

Of the compounds that may form component B, the compounds of formulae II to VI and VII to XII are mentioned and described in more detail under the following common names in "Pesticide Manual" (9th edition, Nov. 1990) on the pages indicated:

| | |
|---|---|
| compound II | Ethofenprox (p. 355) |
| compound III | Cycloprothrin (p. 196) |
| compound IV | Fenobucarb (p. 371) |
| compound V | Isoprocarb (p. 504) |
| compound VI | Metolcarb (p. 586) |
| compound VIII | Monocrotophos (p. 597) |
| compound IX | Cypermethrin (p. 208–209) |
| compound X | Cyhalothrin (p. 201) |
| compound XI | Buprofezin (p. 105) |
| compound XII | Imidacloprid (p. 491) |

The compound of formula VII is known from "Proceedings of the first Asia-Pacific conference of Entomology" p. 42 and 55 ff (1989).

The compounds of formulae XIII and XIIIa are described in published EP Patent Application No. 302.389.

The compound of formula XIV is described in PCT Patent Application WO 91/04965.

The synergistic composition according to the invention is suitable for controlling insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and also representatives of the order Acarina.

The good pesticidal activity of the composition according to the invention corresponds to a mortality of at least 50-60% of the mentioned pests.

The synergistic composition according to the invention can be used especially against sucking plant-destructive insects. Special mention is to be made of the activity of the composition against plant-destructive cicadas, especially against those which attack rice crops, for example cicadas of the families Delphacidae (which includes the genera Nilaparvata and Laodelphax) and Cicadellidae (which includes the genus Nephotettix), such as Nilaparvata lugens, Laodelphax striatellus, Nephotettix cincticeps and Nephotettix virescens. The present composition is also suitable for controlling so-called white-flies (family Aleyrodidae, including, for example, the genera Bemisia and Trialeurodes with the important pest species Bemisia tabaca and Trialeurodes vaporariorum), which are difficult to control.

The composition according to the invention can also be used for controlling plant-destructive plant-eating insects in ornamentals and crops of useful plants, especially in cotton crops (for example against Spodoptera littoralis and Heliothis virescens) and in cereal, fruit and vegetable crops (for example against Laspeyresia pomonella, Lobesia botrana, Adoxophyes orana and A. reticulana and Epilachna varivestis). The composition is distinguished especially by good activity against larval insect stages, nymphs and also eggs, especially of noxious plant-eating insects.

The composition according to the invention can be used for controlling the above-mentioned noxious insects either by using a combination preparation, in which case the two components A and B of the composition according to the invention are applied simultaneously, or by applying the two components A and B shortly after each other. Simultaneous application by the use of a so-called tank mixture prepared by formulating a common, dilute spray mixture of the individually preformulated components A and B is also possible. However, with regard to application safety and reliability of action it is advantageous to use a common formulation of the two components, which the user must simply dilute with water to the application concentration.

According to the invention, components A and B are combined for application, or in the compositions according to the invention, in such ratios that the biological effects are increased synergistically when the two components act in combination. In general, the ratios by weight of A to B are in the range of from 1:1000 to 2:1. Ratios of from 1:20 to 1:1, especially from 1:3 to 1:5, are preferred. In the case of combined application (sum of A+B), preferred application concentrations in the application suspension are generally from 10 to 60 g of active ingredient per 100 l of ready-for-use suspension. Preference is given to a range in which from 20 to 40 g of the active ingredient mixture are applied per 100 l of suspension or in the form of dusts. In the case of application to crops of useful plants, from 10 to 1000 g of active ingredient mixture are applied per hectare, preferably from 100 to 450 g/ha.

When the composition according to the invention is formulated, components A and B are generally used together with the carriers and/or adjuvants conventionally employed in formulation technology and can therefore be formulated in known manner e.g. into emulsifiable concentrates, directly sprayable or dilutable solutions, dilute emulsions, wettable powders, soluble powders, dusts, granules, and also encapsulations in polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures comprising the combinations of A and B and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the $C_8$ to $C_{12}$ fractions of alkylbenzenes such as xylene mixtures or alkylated naphthalenes, aliphatic or cycloaliphatic hydrocarbons, such as cyclohexane, paraffins or tetrahydronaphthalene, alcohols such as ethanol, propanol or butanol, and glycols and their ethers and esters, such as propylene glycol, dipropylene glycol ether, ethylene glycol, ethylene glycol monomethyl or monoethyl ether, ketones, such as cyclohexanone, isophrone or diacetone alcohol, strongly polar solvents, such as N-methyl-2-pyrrolidone, dimethyl sulfoxide or dimethylformamide, or water, vegetable oils, such as rape oil, castor oil, coconut oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are calcite or sand. In addition, a great number of granulated materials of inorganic or organic nature can be used, e.g. especially dolomite or pulverised plant residues.

Suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$-alkyl radical, which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$-alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described, for example, in the following publications:

"McCutcheon's Detergents and Emulsifiers Annual", MC Publishing Corp., Glen Rock, N.J., USA, 1988, H. Stache, "Tensid-Taschenbuch", 2nd edition, C. Hanser Verlag, Munich, Vienna 1981, M. and J. Ash, "Encyclopedia of Surfactants", Vol. I-III, Chemical Publishing Co., New York, 1980-1981.

The compositions according to the invention usually comprise 0.1 to 99%, preferably 0.1 to 95%, of the synergistic active ingredient combination, 1 to 99.9% of a solid or liquid adjuvant, and 0 to 25%, preferably 0.1 to 25%, of a surfactant. Whereas commercial products will preferably be formulated as concentrates, the end user will normally employ dilute formulations which have considerably lower active ingredient concentrations (application concentrations).

Preferred formulations have especially the following composition (throughout, percentages are by weight; active ingredient mixture = components A + B):

| Emulsifiable concentrates: active ingredient | |
|---|---|
| mixture: | 1 to 90%, preferably 5 to 20% |
| surfactant: | 1 to 30%, preferably 10 to 20% |
| liquid carrier: | 5 to 94%, preferably 70 to 85% |
| Dusts: active ingredient | |
| mixture: | 0.1 to 10%, preferably 0.1% |
| solid carrier: | 99.9 to 90%, preferably 99.9 to 99% |
| Suspension concentrates: active ingredient | |
| mixture: | 5 to 75%, preferably 10 to 50% |
| water: | 94 to 24%, preferably 88 to 30% |
| surfactant: | 1 to 40%, preferably 2 to 30% |
| Wettable powders: active ingredient | |
| mixture: | 0.5 to 90%, preferably 1 to 80% |
| surfactant: | 0.5 to 20%, preferably 1 to 15% |
| solid carrier: | 5 to 95%, preferably 15 to 90% |
| Granules: active ingredient | |
| mixture: | 0.5 to 30%, preferably 3 to 15% |
| solid carrier: | 99.5 to 70%, preferably 97 to 85% |

The compositions may also comprise further auxiliaries such as stabilizers, for example vegetable oils or epoxidised vegetable oils (epoxidised coconut oil, rape oil or soybean oil), antifoams, for example silicone oil, preservatives, viscosity regulators, binders, tackifiers as well as fertilisers or other active ingredients for obtaining special effects.

The following Examples serve to illustrate the invention, but do not limit the invention.

EXAMPLE 1

| Wettable powders | a) | b) | c) |
|---|---|---|---|
| active ingredient mixture of components A and B (1:5) | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 62% | 27% | — |

The active ingredient combination is mixed with the adjuvants and the mixture is thoroughly ground in a suitable mill, affording wettable powders which can be diluted with water to give suspensions of the desired concentration.

| Emulsifiable concentrate | |
|---|---|
| active ingredient mixture A and B (1:4) | 10% |
| octylphenol polyethylene glycol ether (4-5 mol of ethylene oxide) | 3% |
| calcium dodecylbenzenesulfonate | 3% |
| castor oil polyethylene glycol ether (36 mol of ethylene oxide) | 4% |
| cyclohexanone | 30% |
| xylene mixture | 50% |

Emulsions of any desired concentration can be produced from this concentrate by dilution with water.

| Dusts | a) | b) | c) | d) |
|---|---|---|---|---|
| active ingredient mixture A and B (1:5) | 5% | 8% | 0.1% | 0.3% |
| talcum | 95% | — | 99.9% | — |
| kaolin | — | 92% | — | 99.7% |

Ready-for-use dusts are obtained by intimately mixing the active ingredient combination with the carrier and grinding the mixture in a suitable mill.

| Extruder granules | |
|---|---|
| active ingredient mixture A and B (1:5) | 10% |
| sodium lignosulfonate | 2% |
| carboxymethylcellulose | 1% |
| kaolin | 87% |

The active ingredient combination is mixed and ground with the adjuvants and the mixture is moistened with water. The mixture is extruded, granulated and then dried in a stream of air.

| Coated granules | |
|---|---|
| active ingredient mixture A and B (1:3) | 3% |
| polyethylene glycol (mol. wt. 200) | 3% |
| kaolin | 94% | the finely ground active ingredient combination is uniformly applied, in a mixer, to the kaolin moistened with polyethylene glycol. Non-dusty coated granules are obtained in this manner.

| Suspension concentrate | a) | b) | c) |
|---|---|---|---|
| active ingredient mixture A and B (1:5) | 40% | 50% | 60% |
| ethylene glycol | 10% | 10% | 8% |
| nonylphenol polyethylene glycol ether (15 mol of ethylene oxide) | 6% | 6% | 5% |
| sodium lignosulfonate | 10% | 10% | 5% |
| carboxymethylcellulose | 1% | 1% | 1% |
| silicone oil in the form of a 75% of aqueous emulsion | 1% | 1% | 1% |
| water | 32% | 22% | 20% |

The finely ground active ingredient combination is intimately mixed with the adjuvants, giving a suspension concentrate from which suspensions of any desired concentration can be obtained by dilution with water.

EXAMPLE 2

Action against rice cicadas-field test 36 m² rice plots in which approximately 3-month-old developed rice plants are growing are infested artificially with Nilaparvata lugens and Nephotettix cincticeps. To that end, parts of plants infested with those rice cicadas are placed in the rice plots to be treated. When complete infestation has occurred, the plots are treated with the insecticidal active ingredients or active ingredient combinations formulated as dusts. Evaluation is made two and 39 (Nilaparvata) or 7 (Nephotettix) days after application of the active ingredient by determining with the aid of a counting device the number of nymphs, larvae and adults of the cicada population that are still mobile, as compared with untreated controls (% activity). These field tests are carried out using three parallel batches per test organism and active ingredient or active ingredient combination.

The results obtained are shown in Table II below:

TABLE II

| Active ingredient used and rate of application | % activity | | Nephotettix after 7 days |
|---|---|---|---|
| | Nilaparvata | | |
| | after 2 days | after 39 days | |
| compound Ia (40 g/ha) | 0% | 58% | 0% |
| compound II (200 g/ha) | 84% | 0% | 81% |
| mixture of compound Ia (40 g/ha) and compound II (200 g/ha) | 100% | 78% | >90% |

By using the mixture of compound Ia and compound II it is possible to keep the pest attack so low up until the rice harvest that no losses occur, the occurrence in the rice crops of the viral disease "hopper burn", which is transmitted by the cicadas, especially being prevented. With none of the individual components alone is it possible with only a single application to achieve the protective effect that is obtained in the sense of complete protection of the rice harvest.

EXAMPLE 3

Action against Nilaparvata lugens-field test

Under the conditions of the preceding Example 2, synergistic mixtures of compound Ia with compounds II and IV are tested, with the difference that active ingredients formulated as emulsifiable concentrates are used instead of dusts (cf. page 13). The aqueous spray mixture is applied by means of a conventional spraying device.

The results obtained are shown in Table III below:

TABLE III

| Active ingredient used and rate of application | % activity against Nilaparvata | |
|---|---|---|
| | after 2 days | after 14 days |
| compound Ia (30 g/ha) | 0% | 12% |
| compound II (100 g/ha) | 48% | 48% |
| mixture of compound Ia (30 g/ha) and compound II (100 g/ha) | 72% | 85% |
| compound Ia (60 g/ha) | 0% | 3% |
| compound IV (500 g/ha) | 52% | 58% |
| mixture of compound Ia (60 g/ha) and compound IV (500 g/ha) | 76% | 79% |

EXAMPLE 4

Ovicidal action against Heliothis virescens

Egg deposits of Heliothis virescens on small pieces of filter paper (approximately 50 eggs not more than 24 hours old per piece of filter paper) are placed in petri dishes (diameter: 5 cm) on the base of which there is a layer of a suitable agar-based larval feed. 0.8 ml of an aqueous formulation (prepared from corresponding emulsifiable concentrates) of the active ingredient or active ingredient mixture is then distributed uniformly over the surface of the feed using a pipette. When the aqueous phase has evaporated, a plastics beaker provided with 3 small holes is placed over the petri dishes. The treated eggs are incubated in a climatic chamber in dim light at 28°±2° C. After 4 days evaluation is made of ovicidal activity, and after 7 days evaluation is made of larvicidal activity and of the inhibition of the development of the larvae.

The results obtained in comparison with untreated controls are shown in Table IV below:

TABLE IV

| Active ingredient used | active ingredient concentration(s) [ppm] ($\approx LC_{50}$) | % activity against Heliothis virescens | |
|---|---|---|---|
| | | ovi-cidal | inhibition of larval development |
| compound Ia | 0.05 | 0% | 40% |
| compound II | 6.0 | 30% | — |
| mixture of comp. Ia + comp. II | 0.05 + 5.0 | 70% | — |
| compound IV | 0.12 | 0% | 65% |
| mixture of comp. Ia + comp. IV | 0.05 + 0.10 | 70% | 100% |
| compound V | 25.0 | 0% | 50% |
| mixture of comp. Ia + comp. V | 0.05 + 25.0 | 65% | 100% |
| compound XII | 12.5 | 50% | 60% |
| mixture of comp. Ia + comp. XII | 0.05 + 10.0 | 85% | 100% |

It can be seen from the results given above that significant synergistic increases in activity can be achieved. Of great practical importance is the 100% inhibition of the development of larvae that is possible with the synergistic mixtures at very low active ingredient concentrations.

EXAMPLE 5

Quantitative determination of synergistic effect-ovolarvicidal activity against Heliothis virescens The test procedure of Example 4 is used as the experimental basis for the quantitative determination of the synergism activity for mixtures of compound Ia as component A with compounds II, IV, XII and XIIIa as component B.

First the % activity as a function of the active ingredient concentration is determined for each individual active ingredient in comparison with untreated controls. The corresponding concentration-mortality curves are calculated from the resulting measured data by means of Probit analysis according to D. J. Finney (Probit Analysis, 2nd edition, Cambridge University Press, 1952). The $LC_{50}$ values (concentration that brings about 5% mortality of the test population) for the individual substances can be found from those curves as follows:

TABLE V

| Compounds | $LC_{50}$ [ppm] | |
|---|---|---|
| | Inhibition of development | ovicidal |
| Ia | 0.02 | 1.53 |
| II | — | 7.05 |
| IV | 0.168 | — |
| XII | 10.4 | — |
| XIIIa | 13.14 | — |

The individual substances are then mixed in proportion to their respective $LC_{50}$ values. The $LC_{50}$ values of these mixtures are also determined as indicated above:

TABLE VI

| Mixture of compounds | $LC_{50}$ [ppm] | |
|---|---|---|
| | Inhibition of development | ovicidal |
| Ia + II | — | 5.71 |
| Ia + IV | 0.055 | — |
| Ia + XII | 4.2 | — |
| Ia + XIIIa | 4.13 | — |

Evaluation

With the aid of these $LC_{50}$ values, the potentiating rate (PR) is determined as a measure of the synergism that occurs, by means of the Cotox formula according to L. Banki (Bioassay of Pesticides in the Laboratory Research and Quality Control, p. 313, Akadémia Kiadó, Budapest, 1978).

The potentiating rate (PR) is calculated from the following quotient:

$$PR = \frac{\widehat{LC_{50}}(A + B)}{LC_{50}(A + B)}$$

In the denominator, $\widehat{LC_{50}}(A+B)$ represents the value for the active ingredient mixture of A and B obtained from the pesticidal test, while the numerator $$\widehat{LC_{50}}(A + B)$$

indicates the expected value for that mixture, which is obtained using the following equation:

$$LC_{50}(A + B) = \frac{1}{\frac{\mu_A}{LC_{50}A} + \frac{\mu_B}{LC_{50}B}}$$

The values $\mu_A$ and $\mu_B$ represent the relative proportion of the relevant mixture component in the total mixture (mixture in proportion to the respective $LC_{50}$ values). The sum of the values $\mu_A$ and $\mu_B$ is 1.

PR values greater than one indicate potentiating increase in activity between the components of the mixture:

TABLE VII

| Mixture of compounds | $\widehat{LC_{50}}$ | Potentiating rate PR | |
|---|---|---|---|
| | | Inhibition of development | ovicidal |
| Ia + II | 6.98 | — | 1.22 |
| Ia + IV | 0.08 | 1.45 | — |
| Ia + XII | 5.10 | 1.22 | — |
| Ia + XIIIa | 6.62 | 1.60 | — |

As can be seen from Tables V and VI together with regard to compound XIIIa, the mixture of XIIIa, for example, with Ia in a concentration ratio of 1:0.0015 leads to an $LC_{50}$ value for the mixture of 4.13 ppm, which corresponds to approximately one third of the $LC_{50}$ value of pure XIIIa (=13.14 ppm).

EXAMPLE 6

Contact action against Bemisia tabaci

Potted dwarf bean plants (untreated) are populated with Bemisia tabaci (white-fly) (40 unsexed adults per plant). The test insects are held on the plants in plastics cylinders. For a period of two days after oviposition has taken place, all adults present are removed. Ten days after removal of the adults, i.e. at a time when approximately 80% of the nymphs are in the second nymphal stage, the populated plants are sprayed to drip point with an aqueous emulsion formulation of the test composition according to the invention (concentration: 400 ppm). Evaluation is made 14 days after application of the active ingredient by determining the % reduction in hatching (=% activity) in comparison with untreated controls. The test is carried out in a climatic chamber at 26° C., at approximately 50% relative humidity, and with a 14-hour light period (10 000 lux).

The composition according to the invention exhibits good synergistic activity in this test.

EXAMPLE 7

Ovicidal action against Cydia pomonella, Adoxophyes reticulana and Lobesia botrana Strips of paper containing egg deposits not more than 24 hours old of the above fruit pests are cut so that each cut piece of paper contains approximately 50 eggs of a pest species. The pieces of paper containing the eggs are then immersed three times for a few seconds in an aqueous emulsion formulation comprising 400 ppm of the test composition according to the invention. After the test formulation has dried, the eggs are placed in petri dishes (diameter: 5 cm) and kept at a temperature of approximately 26° C. and 80% relative humidity, with a light period of 14 hours (approximately 2000 lux). The treated egg deposits of Cydia pomonella (codling moth) are placed between two round paper filters in the petri dish. The egg deposits of Adoxophyes reticulana (summer fruit tortrix moth) and Lobesia botrana (vine moth) are placed between two round cloth filters beneath the cover of the petri dish, into the bottom part of which a normal Lepidoptera feed has been poured. Evaluation is made 6 days later by determining the percentage of larvae which have hatched from the treated eggs in comparison with untreated controls (% reduction in hatching rate).

The composition according to the invention exhibits good synergistic activity in this test.

EXAMPLE 8

Action against Heliothis virescens (caterpillars)

Young soybean plants are sprayed with an aqueous emulsion comprising 400 ppm of the composition according to the invention. After the spray coating has dried, the soybean plants are populated with 10 Heliothis virescens caterpillars in the first stage and placed in a plastics container. Evaluation is made 6 days later. The percentage reduction in the population and the percentage reduction in feeding damage (% activity) is determined by comparing the number of dead caterpillars and the feeding damage on the treated plants with that on untreated plants.

The composition according to the invention exhibits good synergistic activity in this test.

EXAMPLE 9

Action against Spodoptera littoralis (caterpillars)

Young soybean plants are sprayed with an aqueous emulsion comprising 400 ppm of the composition according to the invention. After the spray coating has dried, the soybean plants are populated with 10 Spodoptera littoralis caterpillars in the third stage and placed in a plastics container. Evaluation is made 3 days later. The percentage reduction in the population and the percentage reduction in feeding damage (% activity) is determined by comparing the number of dead caterpillars and the feeding damage on the treated plants with that on untreated plants.

The composition according to the invention exhibits good synergistic activity in this test.

EXAMPLE 10

Action against Plutella xylostella (caterpillars)

Young cabbage plants are sprayed with an aqueous emulsion comprising 400 ppm of the composition according to the invention. After the spray coating has dried, the cabbage plants are populated with 10 Plutella xylostella caterpillars in the third stage and placed in a plastics container. Evaluation is made 3 days later. The percentage reduction in the population and the percentage reduction in feeding damage (% activity) is determined by comparing the number of dead caterpillars and the feeding damage on the treated plants with that on untreated plants.

The composition according to the invention exhibits good synergistic activity in this test.

EXAMPLE 11

Action against Crocidolomia binotalis caterpillars

Young cabbage plants are sprayed with an aqueous emulsion comprising 400 ppm of the composition according to the invention. After the spray coating has dried, the cabbage plants are populated with 10 Crocidolomia binotalis caterpillars in the third stage and placed in a plastics container. Evaluation is made 3 days later. The percentage reduction in the population and the percentage reduction in feeding damage (% activity) is determined by comparing the number of dead caterpillars and the feeding damage on the treated plants with that on untreated plants.

The composition according to the invention exhibits good synergistic activity in this test.

What is claimed is:

1. An insecticidal or acaricidal composition which contains, in addition to a carrier, a synergistic, insecticidally or acaricidally effective amount of an active ingredient consisting essentially of a mixture of a compound of the formula I

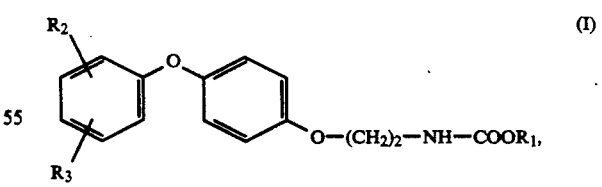

wherein $R_1$ is $C_1$–$C_3$alkyl, $R_2$ halogen and $R_3$ is hydrogen or halogen, and a compound of the formula II

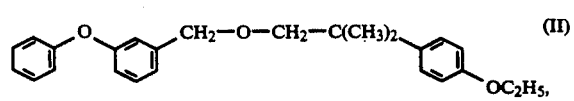

the weight ratio of compound I to compound II being from 1:1000 to 1:1.

2. A composition according to claim 1, which contains the compounds of formulae I and II in a weight ratio of from 1:20 to 1:1.

3. A composition according to claim 2, which contains the compounds of formula I and II in a weight ratio of from 1:3 to 1:5.

4. A composition according to claim 1 which contains a compound of formula I, wherein $R_1$ is $C_1$-$C_3$alkyl, $R_2$ is fluorine or chlorine and $R_3$ is hydrogen or fluorine.

5. A composition according to claim 4 which contains a compound of formula I, wherein $R_1$ is $C_1$-$C_3$alkyl and $R_2$ is 4-fluorine and $R_3$ is hydrogen, or $R_2$ is 3-fluorine and $R_3$ is 5-fluorine, or $R_2$ is 3-chlorine and $R_3$ is hydrogen.

6. A composition according to claim 5 which contains the compound of formula Ia

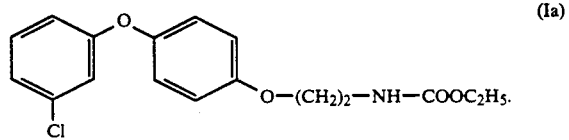

7. A composition according to claim 5 which contains the compound of formula Ib

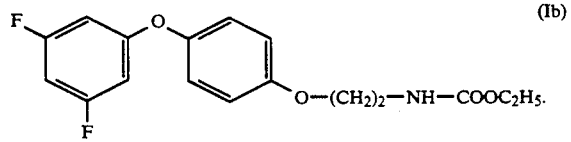

8. A composition according to claim 5 which contains the compound of formula Ic

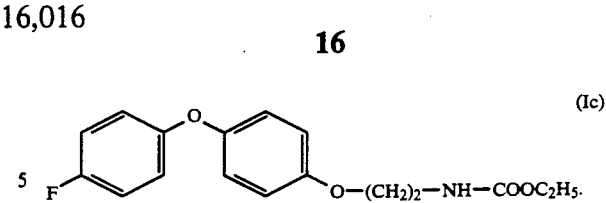

9. A method of controlling pests, selected from the group consisting of insects and representatives of the order Acarina, which comprises treating said pests or their locus with a synergistic insecticidally or acaricidally effective amount of a composition according to claim 1 or with a compound of formula I according to claim 1 and with the compound of formula II according to claim 1, shortly after each other.

10. A method according to claim 9 of controlling insects.

11. A method according to claim 9, wherein the locus to be treated is a crop of useful plants.

12. A method according to claim 10, wherein from 10 to 1000 g of active ingredient are applied per hectare.

13. A method according to claim 11, wherein from 100 to 450 g of active ingredient are applied per hectare.

14. A method according to claim 10 of controlling plant-eating insects.

15. A method according to claim 14 of controlling plant-eating insects in fruit-growing and viniculture.

16. A method according to claim 15 of controlling insects of the genera Adoxophyes, Cydia and Lobesia.

17. A method according to claim 10 of controlling sucking insects.

18. A method according to claim 17 of controlling sucking insects in rice crops.

19. A method according to claim 17 of controlling sucking insects of the genera Bemisia and Trialeurodes.

20. A method according to claim 18 of controlling rice cicadas.

21. A method according to claim 20 of controlling cicadas of the genera Nilaparvata and Nephotettix.

* * * * *